United States Patent [19]
Hamada

[11] 4,103,163
[45] Jul. 25, 1978

[54] INFRARED GAS ANALYZING APPARATUS

[75] Inventor: Toshiyoshi Hamada, Kawasaki, Japan

[73] Assignee: Fuji Electric Co., Ltd., Kawasaki, Japan

[21] Appl. No.: 793,343

[22] Filed: May 3, 1977

[51] Int. Cl.² ............................................. G01N 21/26
[52] U.S. Cl. ..................................................... 250/344
[58] Field of Search ....................... 250/343, 344, 373; 356/51

[56] References Cited

U.S. PATENT DOCUMENTS

| 3,950,644 | 4/1976 | Blunck | 250/343 |
| 3,968,369 | 7/1976 | Luft | 250/344 |

*Primary Examiner*—Davis L. Willis
*Attorney, Agent, or Firm*—Sughrue, Rothwell, Mion, Zinn and Macpeak

[57] ABSTRACT

An infrared gas analyzer includes side-by-side measuring and comparison vessles S, V containing sample and reference gases alternately exposed to infrared light through a rotary chopper CH. The end windows of the vessels are transparent, and a detector D containing two series chambers D1, D2 filled with a gas of the same kind as the component gas to be analyzed is axially disposed below the vessels. A capacitive diaphragm sensor is coupled between the chambers to detect pressure variation differences therebetween, and an adjustable reflecting means is disposed below the transparent bottom window of the second chamber to reflect back a portion of the light energy passing therethrough. The degree of reflection is suitably adjusted so that any interference gas component has an equal influence on the absorption curves of both chambers, whereby its effects are self-cancelling.

The same structural concept of an adjustable reflecting means disposed below the bottom window of the second chamber may also be used to implement zero adjustment when a reference gas is circulated through the vessel.

14 Claims, 20 Drawing Figures

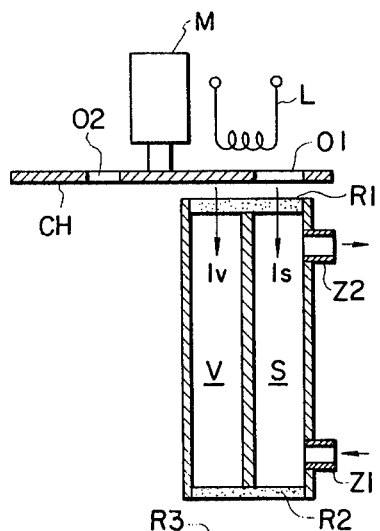
FIG. 1 PRIOR ART
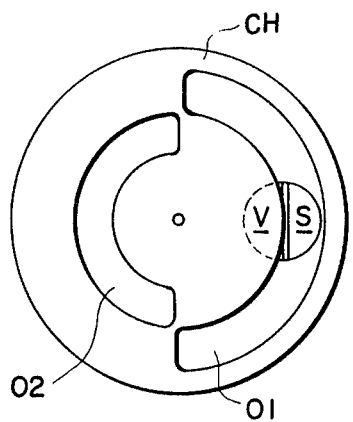
FIG. 2 PRIOR ART
FIG. 3
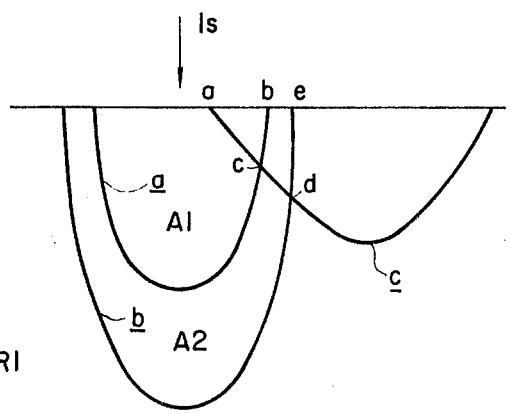
FIG. 4
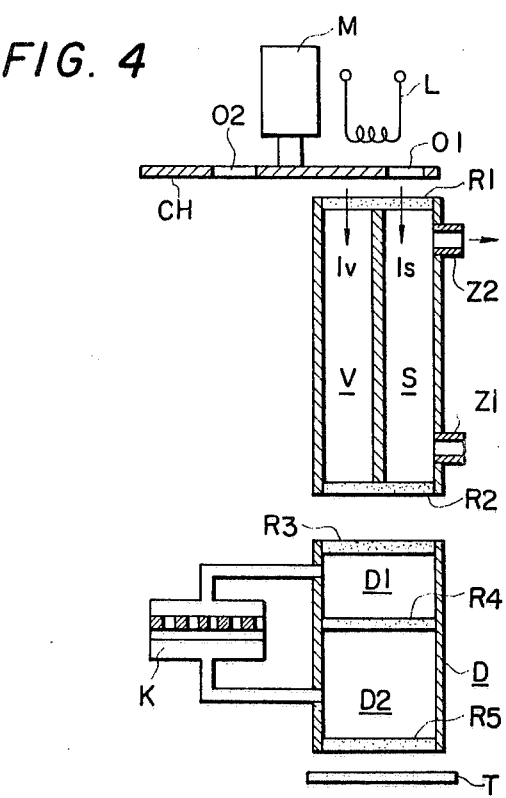

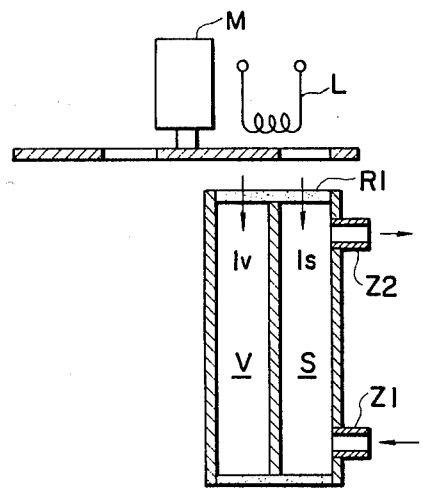
FIG. 9
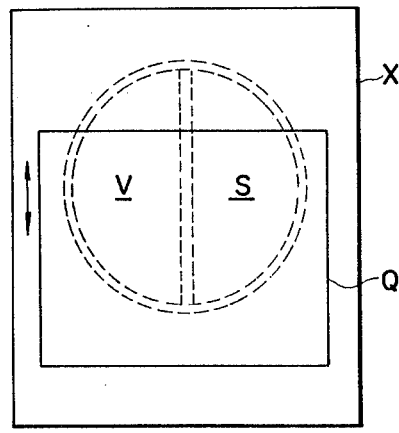
FIG. 10
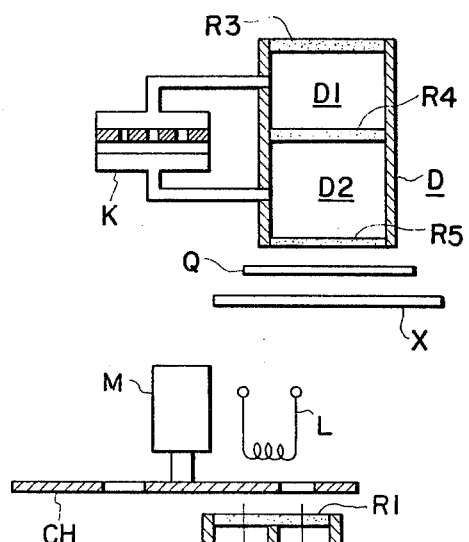
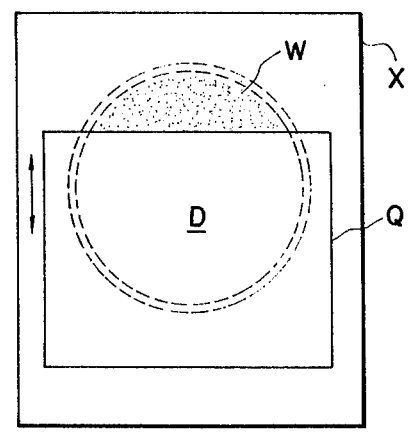
FIG. 11
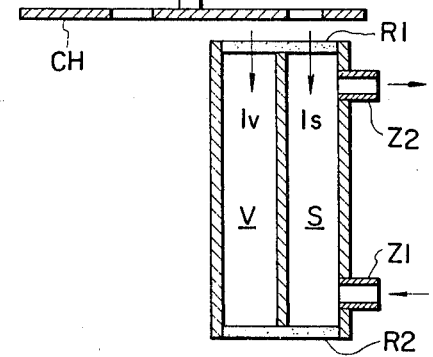
FIG. 12
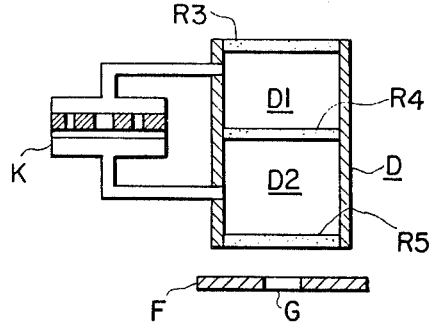

INFRARED GAS ANALYZING APPARATUS

BACKGROUND OF THE INVENTION

This invention relates to an infrared gas analyzing apparatus of the type wherein first and second gas-filled detecting chambers arranged in series are commonly disposed in the path of light measurement rays and light comparison rays, and a gas sample introduced in a vessel disposed in the light measuring path is analyzed by measuring the difference between the light energies absorbed by the first and second detecting chambers, respectively, and wherein the effects of an interference component in the sample, such as water vapor, are compensated for. The invention is also applicable to implement zero adjustment using a reference gas circulated through a vessel.

An example of a prior art infrared ray gas analyzer, as disclosed in U.S. Pat. No. 3,162,761, is shown in FIG. 1, where L designates a source of infrared rays divided by a chopper CH into reference light rays I$\nu$ and measuring light rays I$s$. The chopper CH is rotated by a motor M and has openings O1 and O2, as shown in FIG. 2, wherein opening O1 passes the measuring light rays I$s$ and opening O2 passes the reference light rays I$\nu$.

The measuring and reference light rays are formed by the chopper CH in a periodically alternating manner, the measuring light rays being directed through a measuring vessel S and the reference light rays being directed through a reference vessel V. The vessels S and V are formed in an integral body having light transparent windows R1 and R2 on each end. A sample containing the gas component to be analyzed is introduced into the measuring vessel S through inlet and outlet tubes Z1, Z2, as shown by the arrows, and a gas having no absorbing characteristic for infrared rays, such as nitrogen, is sealed in the reference vessel V. Accordingly, the infrared measuring light rays I$s$ that pass through the vessel S are subjected to absorption depending on the density of the gas component to be analyzed, while the infrared reference light rays I$\nu$ that pass through the vessel V are not subjected to any absorption. After passing through the measuring and reference vessels, respectively, the alternate light rays I$s$ and I$\nu$ are directed into a detector D.

The detector D has a first detecting chamber D1 and a second detecting chamber D2 arranged in series with respect to the paths of the infrared rays, and both of these chambers are filled with a gas of the same kind as the component gas to be analyzed. R3 and R4 designate light transparent windows, and K designates a condenser microphone type of detector connected between the chambers D1 and D2. The difference in pressure variation in the two chambers based on the difference in their infrared ray absorption of the measuring light rays I$s$ is sensed by the condenser microphone K as a capacity variation, and this is appropriately converted into a corresponding voltage variation which indicates a value of the component gas being analyzed.

FIG. 3 shows the energy absorbing characteristics of the measuring light rays I$s$ in the chambers D1 and D2. The area A1 defined by and within curve $a$ indicates the magnitude of the measuring light ray energy absorbed in chamber D1, and the area A2 defined by and between the curves $a$ and $b$ indicates the magnitude of the measuring light ray energy absorbed in chamber D2. The difference $\Delta A$ between the areas A1 and A2 varies in proportion to the density of the component gas being analyzed contained in the sample gas, and an electrical signal corresponding to $\Delta A$ is generated by the electrical circuit including the condenser microphone. The difference $\Delta A$ is always constant when the density of the gas component being analyzed is constant.

In many cases, however, a gas having an infrared-ray absorbing range identical with or partially overlapping that of the gas component being analyzed coexists in the sample gas, and due to this interference component an error is introduced into the analysis results. In FIG. 3 the curve $c$ represents the absorption of infrared rays due to such an interference component. The absorption of infrared rays in the detector D by the interference component affects both of the magnitude of the light energy (area A1) absorbed in chamber D1 and the magnitude of the light energy (area A2) absorbed in chamber D2. When the ratio between the areas A1 and A2 is set such that the area $abc$ is equal to the adjacent area $bcde$, the difference $\Delta A$ between areas A1 and A2 remains constant regardless of the absorption of infrared rays by the interference component, thus eliminating the harmful effects thereof. To suitably select the ratio between the absorption characteristic of the chambers D1 and D2 a procedure is used which includes determining the density of the gas filling the chambers, and the shape and volume of the respective chambers. According to this procedure, however, precise determinations are extremely difficult and the realization of all of the factors and conditions involved is quite complex.

A further prior art infrared ray gas analyzer is disclosed in U.S. Pat. No. 2,951,939, wherein a single measuring vessel S is employed and a movable light shielding plate is disposed between the detecting chambers D1 and D2 to implement zero adjustment. That is, with a reference gas in the measuring vessel and the chambers dimensioned so that A2>A1, the shielding plate is adjusted to cut off or block a portion of the light energy transmitted through chamber D1 before it enters chamber D2, whereby A2 is reduced until it equals A1. This requires the detecting chambers D1, D2 to be constructed as two separate bodies, however, which is relatively difficult and costly in view of the degree of precision required, and the accurate optical alignment of the separate chambers presents a further problem, as does the mechanical stability of the light shielding plate.

SUMMARY OF THE INVENTION

The present invention overcomes the above described difficulties of the conventional devices, and a primary object thereof is to provide an infrared ray gas analyzing apparatus which eliminates the harmful effects of interference gas components in a simple and expedient manner. This object is achieved by providing a first gas-filled detecting chamber upon which measuring light rays transmitted through a measuring vessel and comparing light rays transmitted through a comparison vessel are both projected and through which such rays are transmitted, a second gas-filled detecting chamber upon which the transmitted rays are projected and through which they are both transmitted, and a movable reflecting plate for reflecting part of said measuring light rays and comparing light rays passed through the second detecting chamber back thereto. The degree of such reflection is adjusted so that the interference gas component has an equal influence on the light energy absorbtion on both the first and second detecting chambers, whereby its adverse effects are self-cancelling.

In lieu of a movable mirror member, the combination of a full area fixed mirror underlying a movable light shield may be used, as well as a fixed mirror having a central aperture of selected size or a fixed full mirror underlying a selectively apertured light shield.

Furthermore, according to the invention the second detecting chamber is so designed that the amount of infrared ray energy absorbed thereby is equal to or less than the amount of such energy absorbed in the first detecting chamber, and by adjusting the reflecting plate the energy absorbed in the second chamber is increased to compensate for the effects of the interference gas component.

A further aspect of the invention resides in providing such an adjustable reflecting means to implement zero adjustment when a reference gas is circulated through the vessel.

BRIEF DESCRIPTION OF THE DRAWINGS

In the drawings:

FIG. 1 shows a sectional schematic diagram of a conventional infrared ray gas analyzer;

FIG. 2 shows a top view of the chopper, reference vessel, and measuring vessel of FIG. 1;

FIG. 3 shows the infrared ray absorbtion characteristics for the analyzer of FIG. 1;

FIG. 4 shows a sectional schematic diagram of an embodiment of the present invention;

FIG. 9 shows a sectional schematic diagram of another embodiment of the present invention;

FIG. 10 shows the relation between the reference vessel, measuring vessel, reflecting plate, and the light-shielding plate in this embodiment;

FIG. 11 shows the relation between the detecting chambers, reflecting plate, and the light-shielding plate;

FIG. 12 shows a sectional schematic diagram of a further embodiment of the present invention;

DETAILED DESCRIPTION OF THE PREFERRED EMBODIMENTS

A first embodiment of the present invention will now be described with reference to FIGS. 4 through 8.

Figure 5:
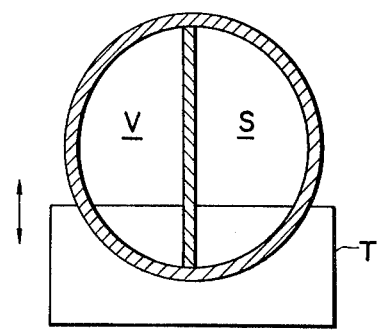
FIG. 5 shows the relation between the reference vessel, measuring vessel, and reflecting plate in the embodiment of FIG. 4.
Figure 6:
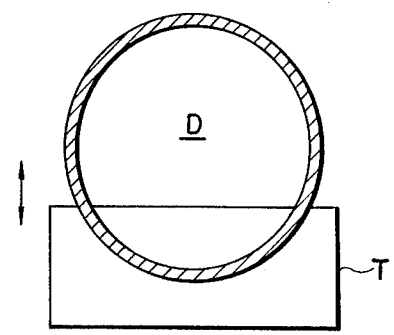
FIG. 6 shows the relation between the detecting chambers and the reflecting plate.

In these drawings the parts having the same structure and function as the corresponding parts in FIG. 1 are designated by the same reference numerals and characters. In this embodiment, another light-transmissible window R5 is provided at the rear or bottom end of the second detecting chamber D2 whereby the infrared rays introduced into the second chamber can pass therethrough. Furthermore, subsequent to or just beyond the second chamber a movable reflecting plate T is disposed so that the infrared rays passed through the second chamber are partially reflected back into it. FIG. 5 shows a top view indicating the relation between the reference vessel V, the measuring vessel S, and the reflecting plate T, and the relation between the detector D and the reflecting plate T is similarly shown in FIG. 6. The sizes of the detecting chambers D1 and D2 are so designed that the infrared ray energy absorbed in the second chamber D2 is less than that absorbed in the first chamber D1. The light rays within the measuring light rays Ls partly reflected back toward the second chamber by the reflecting plate T are termed "reflected light rays" herein.

Figure 7:
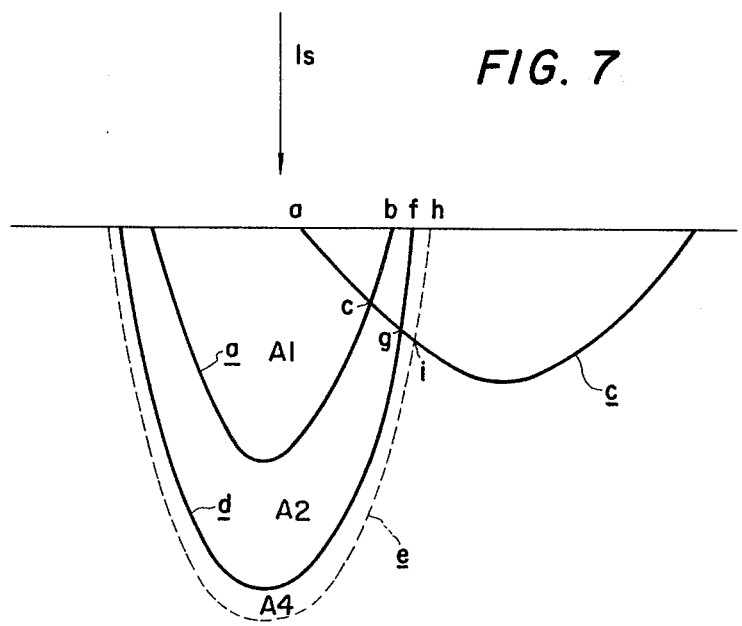
FIG. 7 shows the infrared ray absorbtion characteristics of the detecting chambers.

With reference to FIG. 7, the area A1 surrounded by curve $a$ represents, as in the previous description, the light energy of the measuring light rays Ls absorbed in the detecting chamber D1, and the area A2 defined between curves $a$ and $d$ represents the measuring light ray energy absorbed in the detecting chamber D2. It is assumed that area A1 is greater than area A2, whereby the area $abc$ affected by the absorption of the interference component in area A1 is not equal to the area $bcgf$ affected by such absorption in area A2. Thus, even when the density of the component gas to be analyzed is constant, the difference between the areas A1 and A2 varies depending on the quantity of the interference component.

In order to overcome this difficulty according to the present invention, a movable reflecting plate T is disposed down-stream of the second detecting chamber D2 and part of the energy of the escaping measuring light rays Ls is returned thereby to the second chamber. Curve $e$ represents the light energy absorbing characteristic of the second chamber enlarged by the reflected light rays, and area A4 bounded by curves $d$ and $e$ corresponds to the reflected light ray energy absorbed by the second chamber. As a result, the total infrared ray energy absorbed in the second chamber increases by an amount corresponding to area A4, and such total can be represented by the sum of the areas A2 and A4 (A2 + A4 = A5). The degree of insertion of the reflecting plate T is adjusted so that area $abc$ is made equal to area $bcih$. In this manner if the density of the component gas to be analyzed is held constant, the difference between the areas A1 and A5 is similarly maintained constant regardless of the quantity of the interference gas component, and hence the harmful effects thereof are completely eliminated.

Figure 8:
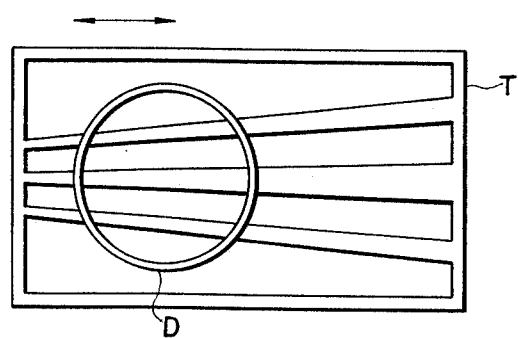
FIG. 8 shows a modified reflecting plate.

FIG. 8 shows a modified reflecting plate T having a tapered strip configuration, and illustrates the relation between such modified reflecting plate and the detector D.

Although only the reflected light energy absorbed in the second chamber D2 has been considered in the above description, some of such reflected light energy is also absorbed in the first chamber D1. The amount of such energy is extremely small, however, and hence the explanation thereof is omitted for the sake of clarity.

In the embodiment of FIG. 9 a reflecting plate X is fixedly disposed to reflect back all of the light rays transmitted through the second detecting chamber D2, and between the reflecting plate X and the second chamber a movable light-shielding plate Q is disposed. The surface of the plate Q on which the light rays are incident is made black to absorb the light rays transmitted through the second chamber, and thereby prevent them from reaching the reflecting plate X.

FIG. 10 shows the relation between the measuring vessel S, the reference vessel V, the light-shielding plate Q, and the reflecting plate X, and FIG. 11 shows the relation between the detector D, the light-shielding plate Q, and the reflecting plate X. As is apparent from FIGS. 10 and 11, the light-shielding plate Q is movable in the direction of the double arrows, whereby only the stippled area W of the reflecting plate X can reflect light rays back toward the second chamber.

Figure 13:
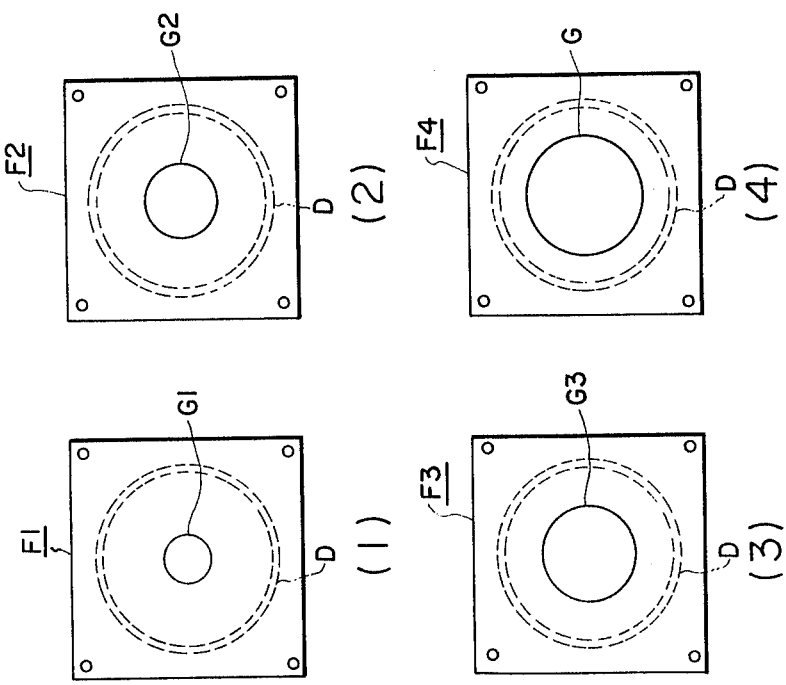
FIGS. 13(1) – (4) show reflecting plates for the embodiment of FIG. 12 having various central aperture sizes, and FIGS. 14(1) – (4) show fixed reflecting plates for the embodiment of FIG. 9 having various shield aperture sizes.

FIG. 12 shows another embodiment of this invention, wherein a reflecting plate F having a central opening G is fixedly disposed downstream of the second detecting chamber. FIGS. 13(1), (2), (3) and (4) show the relationship between the various reflecting plates F1, F2, F3, and F4 and the detecting vessel D, wherein each reflecting plate has a circular opening of different size. Therefore, in adjusting the degree of reflected light, a plate is selected from a plurality thereof to cause the absorption of optical energy by the second chamber to increase to the level shown by curve e in FIG. 7, and the selected plate is then fixedly mounted in the apparatus by a member, not shown.

Figure 14:
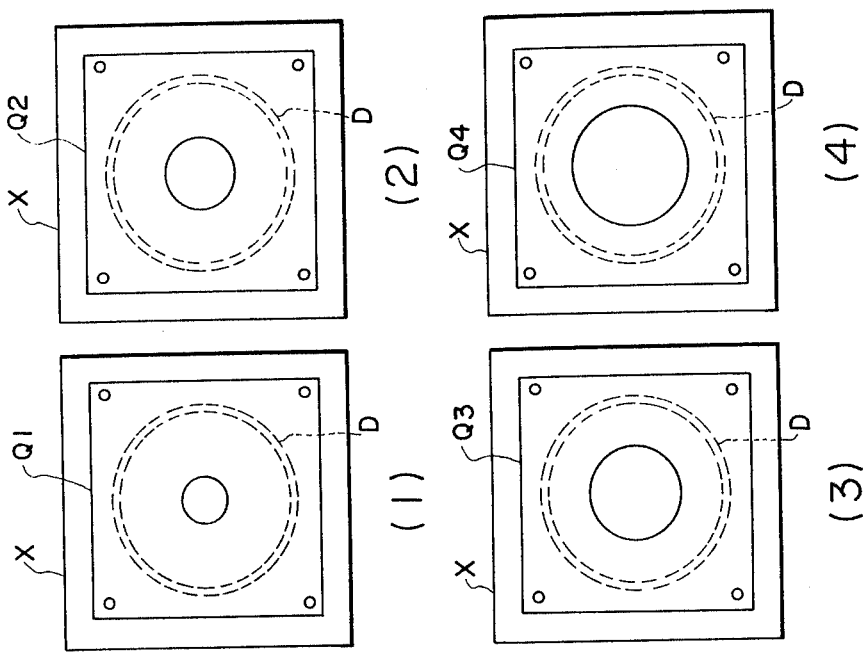

FIGS. 14(1) – (4) show still another plate arrangement, most closely corresponding to the embodiment of FIG. 9. In the latter the shielding plate Q is movable, while the shielding plates Q1, Q2, Q3, or Q4 in FIG. 14 have different size central apertures and a selected plate is fixedly secured to the underlying reflecting plate X.

While not specifically illustrated, the principles of the invention are also applicable to a single vessel apparatus exposed to infrared light through a single window chopper, as in U.S. Pat. No. 2,951,939, but wherein the detecting chambers D1 and D2 are combined, they are dimensioned such that A1 is greater than A2, and the movable light shield between the chambers is replaced by movable reflecting means disposed below the (infrared) transparent bottom window of the second chamber D2. In this manner zero adjustment is easily implemented with a reference gas in the measuring vessel by adjusting the reflecting means to increase the absorbtion in the second chamber until A2 equals A1.

What is claimed is:

1. In an infrared ray gas analyzing apparatus including a measuring vessel for containing a sample or a reference gas and arranged to be intermittently exposed to and transmit therethrough infrared light energy, first and second gas-filled detecting chambers disposed in ordered series after said vessels and axially aligned therewith for absorbing infrared light energy transmitted therethrough, and detecting means coupled between said first and second chambers for sensing pressure variation differences therebetween, the improvements characterized by:
    (a) the end of said second chamber most remote from said vessels being transparent to infrared light energy, and
    (b) adjustable reflecting means disposed after said second chamber end for reflecting a portion of the infrared light energy transmitted through said end back into said second chamber, whereby the degree of reflection may be suitably adjusted such that any interference gas component in a gas sample being analyzed has an equal influence on the absorbtion characteristics of both the first and second chambers, to thereby render its effects self-cancelling.

2. An apparatus as defined in claim 1, further comprising a comparison vessel disposed side-by-side with said measuring vessel for containing a reference gas and arranged to be intermittently exposed to and transmit therethrough infrared light energy, such exposure alternating with the exposure of said measuring vessel, and wherein the reflecting means is disposed and adjustable in such a manner that it always reflects infrared light energy transmitted through both the measuring and comparison vessels to an equal degree.

3. An apparatus as defined in claim 2, wherein said first and second chambers are coaxial and wherein the reflecting means comprises a reflecting plate movable in a direction perpendicular to their common axis.

4. An apparatus as defined in claim 3, wherein the reflecting plate comprises a plurality of spaced, tapered reflecting strips.

5. An apparatus as defined in claim 2, wherein the reflecting means comprises a reflecting plate for reflecting back all of the infrared light energy transmitted through said end, and a movable light shield disposed between said end and said reflecting plate for selectively exposing a desired portion of said reflecting plate.

6. An apparatus as defined in claim 2, wherein the reflecting means comprises a reflecting plate for reflecting back all of the infrared light energy transmitted through said end, and a selected one of a plurality of centrally apertured light shields disposed between said end and said reflecting plate, the apertures in said plurality of light shields being different in size.

7. An apparatus as defined in claim 2, wherein the reflecting means comprises a selected one of a plurality of centrally apertured reflecting plates, the apertures in said plurality of plates being different in size.

8. In an infrared ray gas analyzing apparatus including a measuring vessel for containing a sample or a reference gas and arranged to be intermittently exposed to and transmit therethrough infrared light energy, first and second gas-filled detecting chambers disposed in ordered series after said vessels and axially aligned therewith for absorbing infrared light energy transmitted therethrough, and detecting means coupled between said first and second chambers for sensing pressure variation differences therebetween, the improvements characterized by:
    (a) the end of said second chamber most remoted from said vessels being transparent to infrared light energy, and
    (b) adjustable reflecting means disposed after said second chamber end for reflecting a portion of the infrared light energy transmitted through said end back into said second chamber, whereby the zero adjustment of the apparatus may be implemented by placing a reference gas in the measuring vessel and adjusting the reflecting means until the first and second chambers absorb equal amounts of infrared light energy.

9. An apparatus as defined in claim 8, further comprising a comparison vessel disposed side-by-side with said measuring vessel for containing a reference gas and arranged to be intermittently exposed to and transmit therethrough infrared light energy, such exposure alternating with the exposure of said measuring vessel, and wherein the reflecting means is disposed and adjustable in such a manner that it always reflects infrared light energy transmitted through both the measuring and comparison vessels to an equal degree.

10. An apparatus as defined in claim 9, wherein said first and second chambers are coaxial and wherein the reflecting means comprises a reflecting plate movable in a direction perpendicular to their common axis.

11. An apparatus as defined in claim 10, wherein the reflecting plate comprises a plurality of spaced, tapered reflecting strips.

12. An apparatus as defined in claim 9, wherein the reflecting means comprises a reflecting plate for reflecting back all of the infrared light energy transmitted through said end, and a movable light shield disposed between said end and said reflecting plate for selectively exposing a desired portion of said reflecting plate.

13. An apparatus as defined in claim 9, wherein the reflecting means comprises a reflecting plate for reflecting back all of the infrared light energy transmitted through said end, and a selected one of a plurality of centrally apertured light shields disposed between said end and said reflecting plate, the apertures in said plurality of light shields being different in size.

14. An apparatus as defined in claim 9, wherein the reflecting means comprises a selected one of a plurality of centrally apertured reflecting plates, the apertures in said plurality of plates being different in size.

* * * * *